United States Patent [19]

Forkner

[11] Patent Number: 5,260,495
[45] Date of Patent: Nov. 9, 1993

[54] MONOALKYLENE GLYCOL PRODUCTION USING HIGHLY SELECTIVE MONOALKYLENE GLYCOL CATALYSTS

[75] Inventor: Matthew W. Forkner, Charleston, W. Va.

[73] Assignee: Union Carbide Chemicals & Plastics Technology Corporation, Danbury, Conn.

[21] Appl. No.: 922,002

[22] Filed: Aug. 4, 1992

Related U.S. Application Data

[63] Continuation of Ser. No. 749,332, Aug. 23, 1991, abandoned.

[51] Int. Cl.$^5$ .............. C07C 29/00; C07C 31/20; C07C 33/26; C07C 35/11
[52] U.S. Cl. .................. 568/867; 568/833; 568/811; 568/857

[56] References Cited

U.S. PATENT DOCUMENTS

| | | | |
|---|---|---|---|
| 3,796,792 | 3/1974 | Miyata et al. | 423/250 |
| 3,879,523 | 4/1975 | Miyata et al. | 423/250 |
| 3,879,525 | 4/1975 | Miyata et al. | 423/277 |
| 4,454,244 | 6/1984 | Woltermann | 502/208 |
| 4,458,026 | 7/1984 | Reichle | 502/80 |
| 4,476,324 | 10/1984 | Reichle | 568/388 |
| 4,530,918 | 7/1985 | Sambrook et al. | 502/303 |
| 4,774,212 | 9/1988 | Drezdon | 502/62 |
| 4,883,533 | 11/1989 | Kosin et al. | 106/18.14 |
| 4,967,018 | 10/1990 | Soo et al. | 568/867 |

FOREIGN PATENT DOCUMENTS

| | | |
|---|---|---|
| 207707A2 | 3/1988 | European Pat. Off. . |
| 5569525 | 5/1955 | Japan . |
| 8064525 | 5/1980 | Japan . |
| 57-106631 | 7/1982 | Japan . |

OTHER PUBLICATIONS

Schaper, *Allied Catalysis*, 54: 79–90 (1989).
Reichle, *J. Catalysis*, 94: 547–557 (1985).
Miyata et al., *Chem. Letters*, pp. 843–848 (1973).
Drezdon, *Inorg. Chem.*, 27: 4628–4632 (1988).
Dimotakis, et al., *Inorg. Chem.*, 29: 2393 (1990).

*Primary Examiner*—Marianne M. Cintins
*Assistant Examiner*—Rebecca Cook
*Attorney, Agent, or Firm*—R. M. Allen

[57] ABSTRACT

The invention relates to highly selective, heterogeneous hydrotalcite-type catalysts for the production of monoalkylene glycol by hydrolysis of the corresponding alkylene oxide. The invention also relates to method of preparing these catalysts using large organic anion spacers, and a process for producing monoalkylene glycol.

15 Claims, 1 Drawing Sheet

MONOALKYLENE GLYCOL PRODUCTION USING HIGHLY SELECTIVE MONOALKYLENE GLYCOL CATALYSTS

This application is a continuation of prior U.S. application Ser. No. 07/749,332 filed Aug. 23, 1991, now abandoned.

BACKGROUND OF THE INVENTION

This invention relates to highly selective, heterogeneous catalysts for the production of monoalkylene glycol. The invention also relates to a method of preparing such catalysts and a process for producing monoalkylene glycol using such catalysts.

Commercial processes for preparing alkylene glycols, for example ethylene glycol, propylene glycol and butylene glycol, involve liquid-phase hydrolysis of the corresponding alkylene oxide in the presence of a large molar excess of water (see, for example, Kirk-Othmer, *Encyclopedia of Chemical Technology*, Vol. 11, Third Edition, page 939 (1980)). The hydrolysis reaction typically is conducted at moderate temperatures, e.g., from about 100° C. to about 200° C., and elevated pressures. Water typically is provided to the reaction zone in excess of 15 moles per mole of alkylene oxide. The primary by-products of the hydrolysis reaction include di- and polyglycols, e.g., dialkylene glycol, trialkylene glycol and tetraalkylene glycol. The di- and polyglycols are believed to be formed primarily by reaction of alkylene oxide with alkylene glycol, since alkylene oxide is generally more reactive with alkylene glycol than water. The large excess of water therefore is employed in order to favor the reaction with water and obtain a commercially attractive selectivity to monoalkylene glycol.

Due to the large excess of water used in conventional processes, recovery of alkylene glycol from the hydrolysis reaction mixture is very energy intensive. Water is usually removed from the product stream by evaporation, and the remaining alkylene glycol-containing residue is purified further by distillation. A process which would permit a reduction in the amount of water employed while maintaining or enhancing selectivity toward monoalkylene glycol would reduce energy expenses as well as capital costs.

Many types of soluble or homogeneous catalysts have been proposed for this purpose. For example, U.S. Pat. No. 4,277,632 discloses a process for producing alkylene glycol by hydrolysis of alkylene oxide in the presence of a catalyst containing molybdenum or tungsten. The catalyst may be metallic molybdenum or metallic tungsten, or inorganic or organic compounds thereof, such as oxides, acids, halides, phosphorous compounds, polyacids, alkali and alkaline earth metal compounds, ammonium salts, and heavy metal salts of acids and organic acid salts. Hydrolysis of alkylene oxide takes place in the presence of about one to five times the stoichiometric amount of water without forming appreciable amounts of by-products such as polyglycols. The reaction may be carried out in the presence of carbon dioxide.

Japanese Kokai No. 54/128,507 discloses a process for producing alkylene glycol from alkylene oxide and water using metallic tungsten or tungsten compounds.

Japanese Kokai No. 56/073,035 discloses a process for the hydrolysis of alkylene oxide in the presence of carbon dioxide and a catalyst consisting of a compound containing at least one element selected from the group of titanium, zirconium, vanadium, niobium, tantalum and chromium The compounds include the oxides, sulfides, acids, halides, phosphorous compounds, polyacids, alkali metal salts of acids and polyacids, ammonium salts of acids and polyacids, and heavy metal salts of acids.

Japanese Kokai No. 56/073,036 discloses a process for the hydrolysis of alkylene oxide in the presence of carbon dioxide and a catalyst consisting of a compound containing at least one element selected from aluminum, silicon, germanium, tin, lead, iron, cobalt and nickel.

Japanese Kokai No. 56/92228 is directed to processes for producing highly pure alkylene glycol. A distillation procedure for recovering a molybdenum or tungsten-containing catalyst from an alkylene oxide hydrolysis product in the presence of carbon dioxide is disclosed. The catalyst comprises at least one compound selected from the group consisting of compounds of molybdenum and tungsten, which compound may be in combination with at least one additive selected from the group consisting of compounds of alkali metals, compounds of alkaline earth metals, quaternary ammonium salts and quaternary phosphonium salts. The preferred catalysts are molybdic acid, sodium molybdate, potassium molybdate, tungstic acid, sodium tungstate and potassium tungstate. Potassium iodide is the only additive employed in the examples. For a similar disclosure see, Japanese Kokai No. 56/90029.

U.S. Pat. No. 4,551,566 discloses the production of monoalkylene glycols with high selectivity by reacting a vicinal alkylene oxide with water in the presence of a water-soluble vanadate. Lower water to alkylene oxide ratios can be employed using this process, which results in attractive selectivities to monoalkylene glycol. The counter ion to vanadate is selected to provide a water-soluble vanadate salt under the reaction conditions employed, and alkali metals, alkaline earth metals, quaternary ammonium, ammonium, copper, zinc, and iron are suggested cations. U.S. Pat. No. 4,551,566 also discloses that vanadate may be introduced into the reaction system as a salt or on a support such as silica, alumina, zeolites or clay. Since the vanadate ion is water-soluble, it can be lost from the reaction system. Therefore means must be provided to recover it from the reaction effluent.

In U.S. Pat. No. 4,578,524, the reaction of alkylene oxide and water to form monoalkylene glycol is carried out in the presence of a diassociatable vanadate salt and carbon dioxide.

Although homogeneous catalysts comprising water-soluble salts of vanadate, molybdate, tungstate and other metalates have provided reasonable selectivity to monoalkylene glycol, they are difficult to recover from the hydrolysis products. Accordingly, attention has been directed to the insoluble salts of metalates, which, though more easily recoverable from solutions, traditionally have provided lower selectivities to monoalkylene glycol.

U.S. Pat. No. 4,667,045 discloses the production of alkylene glycol with high selectivity from alkylene oxide and water in the presence of organosalts of a metalate anion having at least one cyclic alkylenedioxy moiety. Particularly preferred metals for the metalate anions are vanadium, molybdenum and tungsten.

European Patent Publication 160,330 describes a process for making alkylene glycols from alkylene oxide and water in the presence of a metalate anion associated with an electropositive complexing site on a solid support, such as an anion exchange resin. Again, metalate anions of the metals vanadium, molybdenum and tungsten are preferred.

Clay minerals belonging to the hydrotalcite-sjogrenite-pyroaurite class have been of interest in preparing insoluble alkylene glycol catalysts. For a general description of these materials, see Reichle, "Catalytic Reactions by Thermally Activated, Synthetic, Anionic Clay Minerals", *Journal of Catalysis*, 94: 547–557 (1985). These clay minerals are composed of infinite layers of metal or nonmetal oxides and hydroxides stacked on top of each other. In cationic clays, these layers are negatively charged and interlayer cations rest in between the layers to neutralize the structure. Anionic clays have positively charged metal oxide/hydroxide layers with anions located interstitially. Many anionic clays contain hydroxides of both main group metals (i.e., Mg, Zn, Al) and transition metals (i.e., Fe, Co, Ni, Cr). The structure of these clays is similar to brucite, $Mg(OH)_2$, in which magnesium ions are octahedrally surrounded by hydroxyl groups with the resulting octahedra sharing edges to form infinite sheets. Some of the magnesium is isomorphously replaced by a trivalent ion, for example $Al_{3+}$. The $Mg_{2+}/Al_{3+}/OH^-$ layers are then positively charged, and insertion of anions into anionic sites between the layers renders the overall structure electrically neutral.

One naturally-occurring, anionic clay is hydrotalcite, in which carbonate ion is present in the interstitial anionic sites. Hydrotalcite has the idealized unit cell formula $Mg_6Al_2(OH)_{16} \cdot CO_3 \cdot 4H_2O$. However, the ratio of Mg to Al in hydrotalcite can vary between 1.7 and 4, and various other divalent and trivalent cations may be substituted for magnesium and aluminum. In addition, the anion may be other than carbonate, and can be changed by synthesis, ion exchange or neutralization.

Hydrotalcite-type compounds have been used in many applications. EPO 207 707 A2 and U.S. Pat. No. 4,454,244 to Woltermann relate to the use of hydrotalcites as ion exchange materials. Schaper, "Stabilized Magnesia: A Novel Catalyst (Support) Material", *Applied Catalysis*, 54: 79–90 (1989) describes the use of hydrotalcites in the double-bond isomerization of 1-pentene. U.S. Pat. No. 4,883,533 to Kosin et al. discusses phosphate-containing hydrotalcites for improving the flame retardant characteristics of plastics and elastomers. JP 80/64,525 relates to the hydrolysis of alkylene carbonates using hydrotalcites. U.S. Pat. No. 4,530,918 to Sambrook et al. describes the use of nickel/aluminum/lanthanum hydrotalcites for use in steam reforming of hydrocarbons.

U.S. Pat. Nos. 3,796,792; 3,879,523 and 3,879,525 to Miyata et al. describe hydrotalcites having both cationic and anionic substitutions. The anionic substitutions may involve $CrO_4^{2-}$, $MoO_4^{2-}$ and $M_2O_7^{2-}$.

U.S. Pat. Nos. 4,458,026 and 4,476,324 to Reichle describe heat treated hydrotalcite for conversion of acetone to mesityl oxide and isophorone and the aldol condensation of other carbonyl-containing compounds. These patents disclose the use of long chain aliphatic alpha-omega dicarboxylates, such as adipic, decane and dodecane dicarboxylates, as interstitial anions.

Reichle, "Catalytic Reactions by Thermally Activated, Synthetic, Anionic Clay Materials", *Journal of Catalysis*, 94:547–557 (1985) describes the effect of varying certain characteristics of hydrotalcite-type materials, and the use of these materials in vapor-phase aldol condensations, acetone oligomerization, and hydrogen-deuterium exchange. Reichle states that the type of anion in the interstitial sites in the hydrotalcite material affects the conversion of acetone to mesityl oxide and isophorone, and the size of the interstitial anion affects the spacing between layers.

Miyata et al., "Synthesis of New Hydrotalcite-like Compounds and Their Physico-chemical Properties", *Chemistry Letters*, pp. 843–848 (1973) relates to hydrotalcites for anion exchange, molecular sieving, and air separation. Miyata et al. describe the relationship between spacing of layers and such characteristics as dehydration temperature, carbon dioxide adsorption and number of carbon atoms in the interstitial anion.

Japanese Kokai No. 55/69525 and Japanese Kokai No. 57/106631 disclose using hydrotalcite and its analogs wherein magnesium is replaced by calcium, zinc, copper or nickel, aluminum is replaced by iron or chromium, and carbonate is replaced by chloride, bromide, fluoride, nitrate, acetate, cyanate, sulfate, chromate, oxalate, phosphate or ferrocyanate, with the stoichiometry adjusted appropriately, as a catalyst for preparing ethylene glycol by reacting ethylene carbonate and water. The disclosures note that these hydrotalcite-type catalysts are easily separated from the liquid reaction medium and are stable under the hydrolysis reaction conditions (130°–160° C.).

U.S. Pat. No. 4,774,212 to Drezdon and Drezdon, "Synthesis of Isopolymetalate-Pillared Hydrotalcite Via Organic-Anion-Pillared Precursors", *Inorganic Chemistry*, 27:4628–4632 (1988) relate to synthesis of hydrotalcites for vapor phase dehydrogenation or ammoxidation of hydrocarbons. These hydrotalcites contain polyoxometalates of vanadium, tungsten and molybdenum as the interstitial anions, and are made by substituting such polyoxometalates into hydrotalcite structures that contain large organic anions.

Dimotakis et al., *Inorganic Chemistry*, 29: 2393 (1990) describes the synthesis of hydrotalcites and other layered double hydroxides containing organic anions using swelling agents such as glycerol.

U.S. Patent No. 4,967,018 to Soo et al. describes a process for the hydrolysis of alkylene oxide to alkylene glycol using hydrotalcite-type mixed-metal framework compositions as catalysts. Soo et al. list a variety of metal cations and interstitial anions that may be used, and disclose that such mixed-metal framework compositions provide particularly high selectivity to monoalkylene glycol when the interstitial anion is selected from metavanadate, orthovanadate, hydrogen pyrovanadate, pyrovanadate, molybdate and tungstate.

Because of the relative desirability of monoalkylene glycol over higher alkylene glycols in the commercial marketplace, it is necessary to employ catalysts in alkylene oxide hydrolysis that are highly selective to monoalkylene glycol. Increases in selectivity to monoalkylene glycol of only a few percentage points translate into large quantities of highly valuable commercial product. Accordingly, the need exists for ways to enhance the selectivity of hydrotalcite-type alkylene oxide hydrolysis catalysts while maintaining catalyst stability (i.e., minimum loss of catalyst constituents such as by leaching). Moreover, since many of the alkylene oxide hydrolysis processes now in commercial use are uncatalyzed, liquid phase processes, it is also desirable for any proposed alkylene oxide hydrolysis catalyst to be retrofittable into current commercial equipment.

SUMMARY OF THE INVENTION

The invention first relates to a process for producing monoalkylene glycol at high selectivities. The process comprises preparing a hydrotalcite-type composition of the formula wherein M is at least one divalent metal cation; Q is at least one trivalent metal cation; A is at least one large organic anion spacer having a valence $n^-$; a is a positive number; M, Q and A are present such that $x/y$ is a number equal to or greater than 1, z has a value greater than zero, $2x+3y-nz$ is a positive number, and the composition has layered structure; A being located in anionic sites of the composition. This hydrotalcite-type composition is contacted with a solution containing a metalate anion, whereby at least some of the large organic anion spacer in the anionic sites is replaced by the metalate anion. Alkylene oxide and water are then reacted in the presence of the metalate-substituted hydrotalcite-type composition to form monoalkylene glycol.

The invention also relates to a method of increasing the selectivity of a hydrotalcite-type catalyst for making monoalkylene glycol. The method comprises preparing a hydrotalcite-type composition of the formula wherein M is at least one divalent metal cation; Q is at least one trivalent metal cation; A is at least one large organic anion spacer having a valence $n^-$; a is a positive number; M, Q and A are present such that $x/y$ is a number equal to or greater than 1, z has a value greater than zero, $2x+3y-nz$ is a positive number, and the composition has a layered structure; A being located in anionic sites in the composition. Metalate anion is then substituted for at least some of the large organic anion spacer in the anionic sites in the hydrotalcite-type composition by contacting the hydrotalcite-type composition with a solution containing the metalate anion. The resulting hydrotalcite-type catalyst exhibits increased selectivity to monoalkylene glycol.

DETAILED DESCRIPTION OF THE INVENTION

Figure 1:
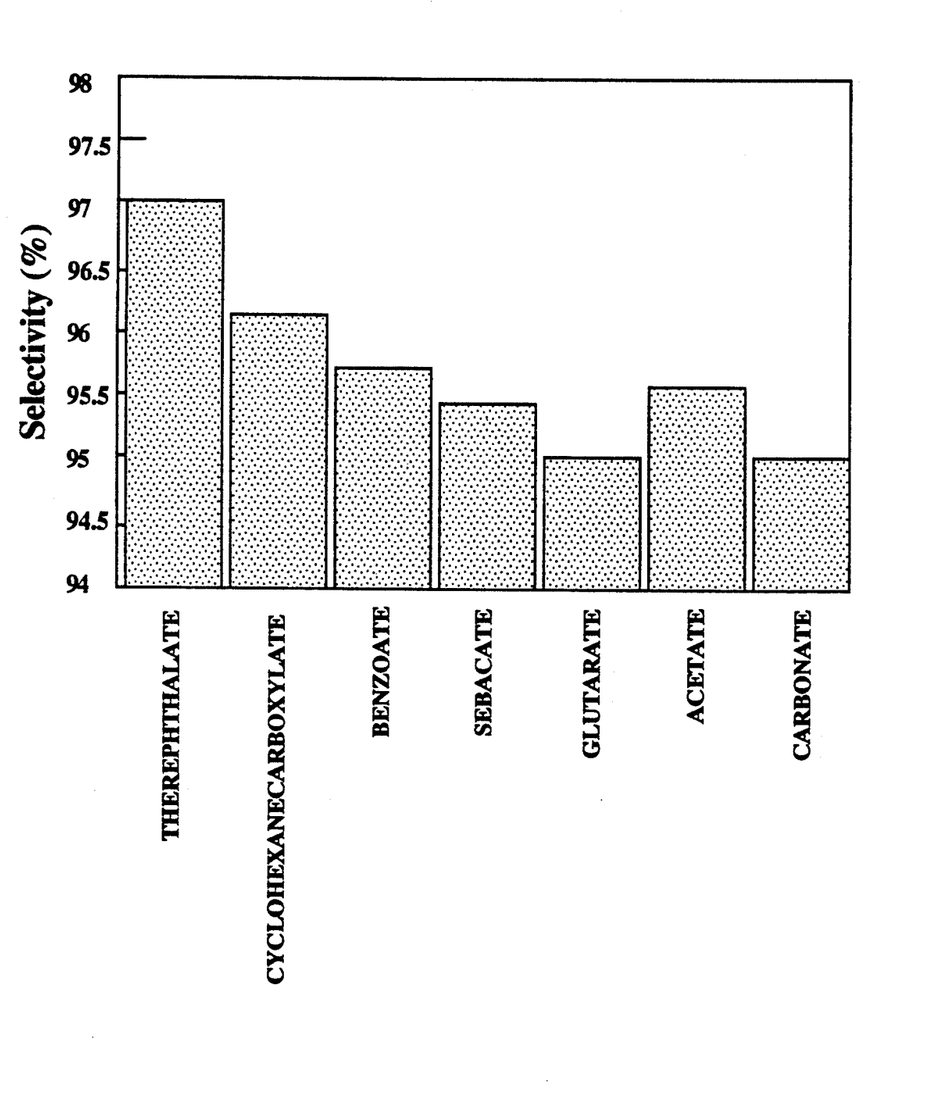
The FIGURE is a graph of large organic anion spacer used versus selectivity to monoethylene glycol.

The invention relates to a process for producing monoalkylene glycol at high selectivities using a hydrotalcite-type catalyst, and a method for increasing the selectivity of such hydrotalcite-type catalyst.

The hydrotalcite-type catalyst of this invention encompasses those compounds of the formula (I)

wherein M is at least one divalent metal cation; Q is at least one trivalent metal cation; E is at least one metalate anion selected from vanadate (metavanadate, orthovanadate, hydrogen pyrovanadate, pyrovanadate), molybdate, tungstate, niobate, tantalate and perrhenate having a valence $n^-$, E being located in anionic sites in the catalyst; a is a positive number; and M, Q and E are present such that $x/y$ is a number equal to or greater than 1, z has a value greater than zero, $2x+3y-nz$ is a positive number, and M, Q and E have such relative atomic sizes that the composition has a layered structure. Preferably, $x/y$ is in the range of 1 to 12, more preferably 1 to 6, and most preferably 1 to 4.

Suitable divalent cations M broadly include elements selected from the transition elements and Groups IIA, IVA and VA of the Periodic Table, as well as certain rare earth elements. Specific examples of divalent metal cations are magnesium, calcium, titanium, vanadium, chromium, manganese, iron, cobalt, nickel, palladium, platinum, copper, zinc, cadmium, mercury, tin, lead and mixtures thereof. Divalent metal cations which are particularly suitable are magnesium, nickel, cobalt, zinc, calcium, iron, titanium and copper.

Suitable trivalent metal cations Q broadly include elements selected from the transition elements and Groups IIIA and VA of the Periodic Table as well as certain rare earth elements and actinide elements. Specific examples of trivalent metal cations are aluminum, antimony, titanium, scandium, bismuth, vanadium, yttrium, chromium, iron, manganese, cobalt, ruthenium, nickel, gold, gallium, thallium, cerium, lanthanum and mixtures thereof. Trivalent metal cations which are particularly suitable are aluminum, iron, chromium, and lanthanum.

The foregoing lists of suitable divalent and trivalent metal cations are meant to be illustrative but not exclusive. Those skilled in the art will recognize that other cations can be used, provided that the types of cations and relative amounts ($x/y$ ratio) result in a hydrotalcite-type catalyst of the desired layered structure in the presence of metalate anion E. In a preferred hydrotalcite-type catalyst, M is nickel, Q is aluminum, E is metavanadate and $x/y$ is in the range of 1 to 6. Another preferred hydrotalcite-type catalyst is formed when M is nickel, Q is aluminum, E is niobate and $x/y$ is in the range of 1 to 6. Hydrotalcite-type materials in which M is nickel and Q is aluminum are known as takovites.

The moieties representing M, Q and E are selected to provide a layered structure in the hydrotalcite-type catalyst. While not wishing to be bound by theory, it is believed that the cation moieties and metalate anion moieties for a particular hydrotalcite-type catalyst generally should have similar sizes in order to provide the layered structure. For instance, because the metalate anions E are typically located in anionic sites between spaced layers of the hydrotalcite-type catalyst, disruptions in the layered structure could occur if metalate anions of substantially different sizes are present the framework.

The catalyst of formula I is prepared according to the invention so as to increase its selectivity to monoalkylene glycol in the hydrolysis of alkylene oxide. Preparation of the catalyst begins with a hydrotalcite-type composition of the formula (II)

wherein M is at least one divalent metal cation; Q is at least one trivalent metal cation; A is at least one large organic anion spacer having a valence $n^-$; a is a positive number; M, Q and A are present such that $x/y$ is a number equal to or greater than 1, z has a value greater than zero, $2x+3y-nz$ is a positive number, and the composition has a layered structure; A being located in anionic sites of the composition. Preferably, $x/y$ is in the range of 1 to 12, more preferably 1 to 6, and most preferably 1 to 4. Preferably z has a value such that x/z is between n and 12n, more preferably between n and 6n, and most preferably between n and 4n.

M and Q in formula II have the same meanings as they do in formula I. Anion A, however is different from metalate anion E. Anion A is a large organic anion spacer, and may be any organic acid containing one to 20 carbon atoms, provided its steric bulk is large. Such organic acid or its alkali salt must be somewhat soluble in a solvent, and may have one or more carboxylic acid functional groups, and may have one or more sulfonic acid functional groups. Large organic anion spacers containing carboxylic acid functional groups are preferred, since these functional groups are readily removed by heating. Preferred large organic anion spacers include terephthalate, benzoate, cyclohexanecarboxylate, sebacate, glutarate and acetate. Preferably, the large organic anion spacer is selected from the group consisting of terephthalate and benzoate. Terephthalate is the most preferred large organic anion spacer. Mixtures of large organic anion spacers may also be used.

The composition of formula II is prepared by mixing, as aqueous solutions, (a) a soluble salt of divalent metal cation M and (b) a soluble salt of trivalent metal cation Q. The resulting cation solution is then mixed with (c) an aqueous solution of a soluble salt of anion A at a temperature of about 25°–35° C. with vigorous stirring over several hours to produce a slurry. The slurry is then heated for about 18 hours at a temperature of from about 50° C. to about 200° C., preferably from about 60° C. to about 75° C., to form crystals. The crystals are filtered, washed and dried. The hydrotalcite-type composition is typically recovered as a powder. Generally the rate of addition of metal cations to the anion solution is not critical and can vary widely. The crystallization temperature is also not critical, although it is preferably kept below about 100° C. An important feature of this mixing procedure is efficient agitation to avoid the formation of undesired by-products. This method of preparing the hydrotalcite-type composition of formula II is set forth in Reichle, "Catalytic Reactions by Thermally Activated, Synthetic, Anionic Clay Minerals", *Journal of Catalysis*, 94:547–557 (1985). See also, U.S. Pat. No. 4,458,026, the disclosure of which is incorporated herein by reference.

Another suitable method of preparing the hydrotalcite-type composition of formula II is found in Schafer, *Applied Catalysis*, 54:79 (1989). Soluble salts of cations M and Q are used as above, however according to this method, a caustic solution containing the desired anion is added quickly to the metal anion salts for very fast mixing, so that the pH of the mixture is controlled. This method produces uniform, small crystals.

Any soluble salts of divalent metal cation M and trivalent metal cation Q may be used according to the invention. For example, nitrates, sulfates, or halides of the metal cations may be used to prepare the composition of formula II. Preferably, nitrates are employed. The large organic anion spacer can be used in the form of a salt or an acid. Alkali metal salts of the large organic anion spacer are especially preferred. If the acid form of the large organic anion spacer is used, it is made up in a solution containing a base, such that the pH of the solution is about 10 or higher. Care must be exercised to exclude carbon dioxide from the reaction medium, since carbonate ion is preferred as the interstitial anion in hydrotalcite-type materials.

The crystallization step also plays an important role in the preparation of the hydrotalcite-type composition of formula II. Absent this step, the product generally comprises a slurry containing essentially amorphous hydroxides. A suitable heat-treating or crystallization period is important for producing solid material with the desired layered structure as characterized by a well-defined X-ray diffraction pattern. Generally, the higher the crystallization temperature and the longer the heating time, the larger the particle size of the resulting crystals.

The hydrotalcite-type composition of formula II also can be prepared from the native or synthetic hydrotalcites by ion exchange. For example, hydrotalcite can be treated at ambient conditions with terephthalic acid for about 18 hours to replace the carbonate anion with terephthalate anion. Similarly, a halide analog of hydrotalcite prepared directly or by anion-exchange could be contacted with benzoic acid or a water soluble salt thereof, in order to substitute the benzoate anion for the halide anion in the structure to produce a hydrotalcite-type composition of formula II. It may be advantageous to use glycerine or a similar compound to help pry apart the layers of the hydrotalcite starting material. Other ion exchanges will be apparent to those skilled in the art.

Further procedures for the preparation of the hydrotalcite-type composition of formula II are provided in Itaya et al., *Inorg. Chem.*, 26:624–626 (1987); Taylor, *Clay Minerals*, 19:591–603 (1984); U.S. Pat. No. 4,476,324; Bish, *Bull. Minerals*, 103:170–175 (1980) and Miyata et al., *Clays and Clay Minerals*, 25:14–18 (1977), the disclosures of which are incorporated herein by reference. Using direct synthesis, one has the ability to vary within wide limits the $M^{+2}/Q^{+3}$ atomic ratio as well as the anion.

In order to prepare the hydrotalcite-type catalyst of formula I having increased selectivity to monoalkylene glycol, the hydrotalcite-type composition of formula II is contacted with a solution containing the desired metalate anion. Suitable metalate anions include metavanadate, orthovanadate, hydrogen pyrovanadate, pyrovanadate, molybdate, tungstate, niobate, tantalate, perrhenate, chromate and manganate. Preferably, any of the vanadates, molybdate or niobate are used. Preferably a stoichiometric excess of metalate anion is employed. Useful compounds of metalate anions for this purpose include alkali metal salts, ammonium salts, tetraalkyl ammonium salts and other soluble salts of metalate anions. Preferably the solution containing the metalate anion is added to an aqueous slurry of the hydrotalcite-type composition of formula II. The pH of the mixture should be maintained in the range of about 9 to 11, such that the metalate anion remains in the monomeric state.

During contacting of the hydrotalcite-type composition with the solution containing the metalate anion, at least some of the large organic anion spacer in the anionic sites in the hydrotalcite-type composition is replaced by the metalate anion. The resulting metalate anion-substituted hydrotalcite-type composition is the hydrotalcite-type catalyst of formula I.

This catalyst exhibits enhanced selectivity to monoalkylene glycol when used in the hydrolysis of alkylene oxide compared with hydrotalcite-type catalysts prepared from hydrotalcite-type compositions without large organic anion spacers. Specifically, Applicant has discovered that the large organic anion spacers in the hydrotalcite-type composition of the invention, which is the precursor to the catalyst, serve as levers to separate the positively charged layers of the composition. Because the positively charged layers are further separated, the large, sterically hindered metalate anions are able to readily enter the structure. Applicant believes that this phenomenon contributes to the increased monoalkylene glycol selectivity of the hydrotalcite-type catalysts prepared according to the invention. In addition, additional space between layers of the hydrotalcite-type catalyst allows greater diffusion of reactants (alkylene oxide) into and products (alkylene glycol) out of the catalyst.

In general, the larger the size of the large organic anion spacer, the higher the selectivity of the hydrotalcite-type catalyst to monoalkylene glycol. For example the FIGURE is a graph of large organic anion spacer used versus selectivity to monoalkylene glycol for a hydrotalcite-type catalyst wherein M is nickel, Q is aluminum and E is vanadate. The FIGURE shows that use of large organic anion spacers having greater steric bulk yields hydrotalcite-type catalysts having higher selectivity to monoalkylene glycol. Use of carbonate anion, the anion which naturally occurs in hydrotalcites, provides a catalyst having a relatively low selectivity to monoalkylene glycol. Applicant has discovered that preparation of hydrotalcite-type catalysts via hydrotalcite-type compositions containing large organic anion spacers increases the monoalkylene glycol selectivity of these catalysts significantly.

According to a preferred embodiment of the invention, the hydrotalcite-type composition of formula II is calcined before it is contacted with the solution containing the metalate anion. Calcination takes place at elevated temperatures, preferably at about 300°-600° C., for about 12-24 hours. Calcination may be performed in air, under an inert atmosphere, or under a vacuum. It is preferred that the calcination temperature not exceed about 600° C., at which point irreversible calcination takes place, i.e., the layered structure of the composition disappears and cannot be regenerated. During calcination, water and at least a portion of the large organic anion spacer are driven off, leaving a layered material having voids in the anionic sites formerly occupied by the large organic anion spacer.

It is not necessary to calcine the composition of formula II, and the invention is directed to the use of either uncalcined or calcined hydrotalcite-type compositions to make the hydrotalcite-type catalyst of the invention. However, increased selectivities are often (but not always) achieved by calcining the hydrotalcite-type composition before it is contacted with the solution containing the metalate anion. Calcining the composition may open up and expose interior anionic sites, such that most of the metalate anions introduced into the hydrotalcite-type composition are placed in anionic sites that are catalytically active.

Loading of the metalate anions into the hydrotalcite-type composition is performed in the same manner whether the composition has been calcined or not, i.e., by contacting the hydrotalcite-type composition with the metalate anions. Surprisingly, Applicant has found that frequently the uncalcined composition absorbs a larger amount of metalate anion than does the calcined composition. Despite this, when the calcined composition is loaded with metalate anion to form the hydrotalcite-type catalyst, a higher selectivity to monoalkylene glycol is achieved. Applicant believes this may in part be due to the fact that calcination results in higher surface areas, and that the majority of hydrolysis reactivity occurs on or near the surface and edges of the catalyst. With uncalcined hydrotalcite-type compositions, at least about 25 molar %, preferably about 50 molar %, of the anionic sites of the composition are loaded with metalate anion. If loading is allowed to proceed for an extended time period, up to 100 molar % of the anionic sites may be loaded with metalate anion. With calcined hydrotalcite-type compositions, at least about 1 molar %, preferably about 5 molar % or more, of the anionic sites are loaded with metalate anion to achieve the superior results of the invention. More preferably, at least about 10-30 molar % of the anionic sites are loaded with metalate anion in the calcined hydrotalcite-type composition.

The finished, dry, hydrotalcite-type catalyst can be used for heterogeneous catalysis as is or can be pelleted or extruded with or without the addition of binder in order to form larger particles more suitable for use in fixed bed reactors, fluid bed reactors, slurry reactors and the like. Some hydrotalcite-type catalysts of the invention, for example those in which the anion is molybdate or vanadate, can be formed into pellets having sufficient structural integrity for some purposes without adding any significant amount of binder. In order to form useful pellets with other hydrotalcite-type catalysts of the invention however, such as those having tungstate as the anion, binder generally is required. The hydrotalcite-type catalyst also may be supported on a suitable carrier. As will be appreciated by those skilled in the art, the use of binder may be desired in certain applications, regardless of the anion.

The catalytic hydrolysis of alkylene oxide using the broad class of hydrotalcite-type catalysts of the invention can be conducted in either the liquid or vapor phase. However, certain hydrotalcite-type catalysts are more suited to either a liquid phase or vapor phase process. In fact, some hydrotalcite-type catalysts exhibit better catalytic activity and selectivity in one process as compared to another.

In accordance with the invention, a mixture of alkylene oxide and water, in either the liquid or vapor state, is contacted with a suitable hydrotalcite-type catalyst to catalyze the hydrolysis of the alkylene oxide selectively to the monoalkylene glycol. In the case of a liquid phase hydrolysis reaction, the process usually is carried out at a temperature from about 20° C. to 250° C., preferably from about 50° C. to 200° C. While the process may be conducted at a variety of pressures, the reaction conveniently is conducted at pressures greater than atmospheric, for example, from about 25 psig to 10,000 psig and preferably from about 25 psig to 1500 psig. Of course, the reaction temperature and pressure are selected to maintain liquid reaction conditions. The PH of the liquid reaction system also can affect both the rate and selectivity of the reactions leading to the desired monoalkylene glycol product. In general, the pH of the liquid reaction system is from about 3 to 13, preferably from about 6 to 9.

In conventional liquid phase hydrolysis systems, alkylene oxide first is recovered from the outlet stream of alkylene oxide reactors by scrubbing and stripping with water. The enriched alkylene oxide stream then is purified and hydrolyzed to glycol. Water in the hydrolysis effluent is removed in a series of multi-effect evaporators. In addition to their capital costs, both the alkylene oxide recovery/refining system and the evaporation train are very energy intensive.

In a vapor phase process, significant economy of operation is possible by conducting the vapor phase hydrolysis at the alkylene oxide reactor outlet and eliminating the alkylene oxide refining system and the evaporation train. A vapor phase hydrolysis process typically is operated at a higher temperature, sufficient under the conditions of pressure and composition to maintain the fluid in the vapor phase during the reaction. Often the temperature is in the range of about 160° C. to 290° C., preferably about 180° C. to 260° C. Reaction pressures from subatmospheric to 750 psig are suitable, while a pressure from 150 psig and 300 psig is preferred. Of course, conditions must be selected which maintain the reactants in the vapor state. A gas hourly space velocity for the vapor phase process may range from about 1000 hr$^{-1}$ to 16,000 hr$^{-1}$, with a value of from 2000 hr$^{-1}$ to 6000 hr$^{-1}$ generally being preferred.

Alkylene oxides suitable for preparing monoalkylene glycols using the process of the invention have the formula wherein $R^1$, $R^2$, $R^3$ and $R^4$ each designate a hydrogen atom, an alkyl group having from 1 to about 10 carbon atoms (preferably from 1 to 4 carbon atoms), an aryl group having at least 6 carbon atoms, (for example, a monocyclic or bicyclic aryl), an alkenyl group having 2 or 3 carbon atoms, or a cycloalkyl group having 3 to 6 carbon atoms, and $R^1$ and $R^3$ may be joined to form a cyclic structure. Representative of the alkylene oxides that may be used in the invention are ethylene oxide, propylene oxide, butylene oxide (including isobutylene oxide, 1,2-butylene oxide and 2,3-butylene oxide), pentylene oxide, cyclohexene oxide, styrene oxide and the like. Preferably, the alkylene oxide is an aliphatic alkylene oxide, such as ethylene oxide or propylene oxide.

Generally, the source of the alkylene oxide is not important. Of course, impurities that may interfere with the formation of monoalkylene glycol or deactivate the hydrotalcite-type catalyst should be removed. For example, ethylene oxide produced by the catalytic oxidation of ethylene with molecular oxygen or an oxygen-containing gas in the presence of a silver catalyst typically is recovered at a high purity and can be suitably employed without any pretreatment.

Water of a sufficient purity to provide the desired quality of monoalkylene glycol also should be used. Normally, in the liquid phase process, from about 1 to about 40 moles of water are used per mole of alkylene oxide. To reduce energy and equipment costs, the molar hydrolysis ratio typically is adjusted to a value from about 1 to 25. A slight molar excess of water over the stoichiometric amount is desired to maintain high selectivity in the conversion of alkylene oxide to monoalkylene glycol. In a vapor phase process, the molar hydrolysis ratio is from about 1 the ratio prevailing at the water vapor saturation pressure under the reaction conditions. Generally, conditions are selected to provide a molar hydrolysis ratio of water to alkylene oxide of from about 1 to 10.

In either liquid or vapor phase processes, the reaction can be carried out in the presence of a diluent gas such as air, argon, nitrogen, methane and the like. Carbon dioxide also may be present during the hydrolysis of the alkylene oxide. In many cases up to about 15 molar percent of carbon dioxide may be inherently present when the alkylene oxide is produced by epoxidation of an alkene. Carbon dioxide in an amount of up to about 6 molar percent may enhance the selectivity provided by certain hydrotalcite-type catalysts of the invention, particularly in connection with vapor phase hydrolysis.

The mass flow of the reactants over the hydrotalcite-type catalyst generally is adjusted so as to provide the desired rate enhancement and selectivity. Preferably, the reaction is conducted for sufficient period of time to ensure maximum conversion of alkylene oxide. The time needed for maximum conversion is a function of a variety of parameters including temperature, amount of reactants, and so forth, and is within the skill of the art.

The process of the invention can be carried out either as a batch or continuous process, with recycle of unconsumed reactants if required. For commercial applications, a continuous process is preferred.

Alkylene glycol may be recovered from the reactor effluent in any convenient manner, e.g., by distillation or condensation, and such procedures are known to those skilled in the art. The hydrotalcite-type catalyst of the invention is hydrothermally stable and solid, and is readily separated from the hydrolysis product stream. In the context of the present invention, the phrase "hydrothermally stable" means that the hydrotalcite-type catalyst of the invention remains active at the elevated temperature conditions of liquid and vapor phase hydrolysis without experiencing an excess loss of catalyst constituents, e.g., by leaching. Typically, when a liquid phase process is used to prepare alkylene glycol, the water recovered with the glycol product is removed in a series of multiple-effect evaporators and the alkylene glycol is further refined by vacuum distillation. One advantage of the vapor phase process is that recovery of alkylene glycol is facilitated significantly since it can be recovered by condensation. Purification of the alkylene glycol can be effected by any convenient means, such as distillation.

Vanadate and niobate are preferred metalate anions for a liquid phase hydrotalcite-type catalyst. Vanadate-containing and niobate-containing catalysts provide a significant degree of selectivity enhancement to monoalkylene glycol. Furthermore, since magnesium has a greater tendency to leach from magnesium-aluminum catalysts than nickel from nickel-aluminum catalysts, vanadate- or niobate-containing nickel-aluminum catalysts are preferred over vanadate- or niobate-containing magnesium-aluminum catalysts.

An especially preferred embodiment of the invention is a hydrotalcite-type catalyst wherein M is nickel, Q is aluminum and E is vanadate or niobate prepared from a hydrotalcite-type composition wherein M is nickel, Q is aluminum and A is terephthalate. The highest selectivities have been achieved with this catalyst when the hydrotalcite-type composition is calcined before contacted with the vanadate or niobate anions. The nickel/aluminum ratio is preferably from about 2 to 4. The amount of vanadate or niobate in the finished catalyst is preferably about 1 to 20 percent by weight of the hydrotalcite-type catalyst.

As an illustration of the increased selectivities achievable according to the invention, in the hydrolysis of ethylene oxide to form monoethylene glycol, at a water to ethylene oxide molar hydrolysis ratio of from about 21 to about 24, a hydrotalcite-type catalyst wherein M is nickel, Q is aluminum, and E is vanadate prepared according to the invention from a hydrotalcite-type composition wherein M is nickel, Q is aluminum and A is terephthalate, gives a selectivity to monoethylene glycol of about 95% or higher at a reaction temperature of 120°-180° C., a pressure of about 200 psig, a catalyst mesh size of about 10–20, and 100% conversion of ethylene oxide. A hydrotalcite-type catalyst wherein M is nickel, Q is aluminum and E is niobate prepared according to the invention from a hydrotalcite-type composition wherein M is nickel, Q is aluminum and A is terephthalate, exhibits a selectivity to monoethylene glycol of about 96.5% at the same hydrolysis reaction conditions.

These selectivities compare very favorably with uncatalyzed hydrolysis reactions, in which the selectivities under similar reaction conditions are typically only about 90%. These selectivities also compare favorably with hydrotalcite-type catalysts having the same metalate anions, but which were prepared from hydrotalcite-type compositions without large organic anion spacers. For example a hydrotalcite-type catalyst wherein M is nickel, Q is aluminum, and E is vanadate prepared from a hydrotalcite-type composition wherein the interstitial anion is naturally-occuring carbonate, has a selectivity to monoethylene glycol of only about 95.1%. Similarly, a hydrotalcite-type catalyst wherein M is nickel, Q is aluminum and E is niobate prepared from a hydrotalcite-type composition wherein the interstitial anion is carbonate has a monoethylene glycol selectivity of only about 95.7%.

A less preferred but still effective hydrotalcite-type catalyst prepared according to the invention is that in which M is titanium, Q is aluminum, and E is vanadate or molybdate. This hydrotalcite-type catalyst may be prepared from a hydrotalcite-type composition wherein M is titanium, Q is aluminum and A is any of the large organic anion spacers of the invention. In the hydrolysis of ethylene oxide to form ethylene glycol at about 160° C., 200 psig and a molar hydrolysis ratio of water to ethylene oxide of about 24:1, this aluminum-titanium-oxyhydroxide catalyst prepared according to the invention would achieve a selectivity to monoethylene glycol of about 93 to 94%.

Commercial rates of monoalkylene glycol production can be obtained in the liquid phase process using either the uncalcined or calcined hydrotalcite-type catalysts. As explained above, calcined hydrotalcite-type catalysts frequently exhibit a higher level of selectivity than uncalcined catalysts, especially in the liquid hydrolysis process. Importantly, if a calcined hydrotalcite-type catalyst experiences any decline in selectivity, it can be regenerated by heat treatment to restore at least partially its initial level of selectivity and reused. Conditions discussed above for calcining the hydrated hydrotalcite-type composition according to the invention are suitable for regenerating a hydrotalcite-type catalyst that has experienced a decline in activity.

Higher selectivity to monoalkylene glycol is particularly important for heterogeneous vapor phase alkylene oxide hydrolysis catalysts. Polyglycols formed with catalysts of lower selectivities may accumulate on the catalyst surface. Such accumulation generally leads to catalyst deactivation and still lower selectivity.

The following non-limiting examples are provided to further illustrate the invention.

EXAMPLE 1

This example illustrates the synthesis of a hydrotalcite-type catalyst according to the invention, wherein M is nickel and Q is aluminum (takovite), and E is vanadate from a hydrotalcite-type composition wherein M is nickel, Q is aluminum and A is terephthalate.

A 3 liter flask was flushed with $N_2$ for 30 minutes, and then equipped with a reflux condenser, temperature probe, mechanical stirrer, pressure equalizing addition funnel and nitrogen inlet. One liter of deionized water, 167 g of low carbonate sodium hydroxide and 75 g of terephthalic acid were charged to the flask. The contents were stirred until dissolved and then cooled to room temperature.

A metal salt solution was prepared by adding 169 g of aluminum nitrate and 291 g of nickel nitrate to deionized water to make a 700 ml solution. The metal salt solution was charged to the addition funnel. The contents of the flask were heated to 40° C. and the metal salt solution was added to the flask with rapid stirring.

The resulting mixture was allowed to digest at 70° C. for 18 hours. It was then cooled to room temperature, suction filtered, washed with 600 ml of deionized water, and air dried. The resulting hydrotalcite-type composition was then calcined at 400° C. overnight, and the fines were separated.

A 3 liter flask was then flushed with $N_2$ for 30 minutes, and the calcined material was added thereto along with 1500 ml of deionized water. The pH was maintained in the range of 9–11. 122 g of sodium metavanadate were added to the flask and stirred gently for 18 hours. The resulting hydrotalcite-type catalyst was suction filtered, washed with deionized water and air dried.

The resulting hydrotalcite-type catalyst was designated Catalyst 1. It was used to catalyze the reaction of ethylene oxide to monoethylene glycol as follows. A solution of water and ethylene oxide (about 22 moles water to 1 mole ethylene oxide) was passed through a stainless steel tube having a diameter of ⅜ inch and a length of 16 inches. Inside the tube was 13.1 g of Catalyst 1. The catalyst was maintained at 160° C. by an oil bath and the pressure was maintained at 200 psig.

Table 1 shows that the monoethylene glycol selectivity achieved with Catalyst 1 was 97.0%.

EXAMPLE 2

Catalyst 2 was prepared and used to catalyze the reaction of ethylene oxide to monoethylene glycol in the same manner as Catalyst 1 in Example 1, except the hydrotalcite-type composition was not calcined before it was contacted with the sodium metavanadate. The monoethylene glycol selectivity of Catalyst 2 was 95.3%, as indicated in Table 1.

EXAMPLE 3

Catalyst 3 was prepared and used to catalyze the reaction of ethylene oxide to monoethylene glycol in the same manner as Catalyst 1 in Example 1, except cyclohexanecarboxylic acid was used instead of terephthalic acid. Catalyst 3 had a monoethylene glycol selectivity of 96.2%, as shown in Table 1.

Catalyst 4 was prepared in the same manner as Catalyst 3, except without the calcination step. Catalyst 4 had a monoethylene glycol selectivity of 95.8%, as shown in Table 1.

EXAMPLE 4

Catalyst 5 was prepared and used to catalyze the reaction of ethylene oxide to monoethylene glycol in the same manner as Catalyst 1 in Example 1, using 80 g of sodium hydroxide, 72 g of sodium benzoate, 124 g of aluminum nitrate, 192 g of nickel nitrate, and 30 g of sodium metavanadate. Catalyst 5 had a monoethylene glycol selectivity of 95.8%, as shown in Table 1.

Catalyst 6 was prepared in the same manner as Catalyst 5, except without the calcination step. Catalyst 6 had a monoethylene glycol selectivity 94.9%, as shown in Table 1.

EXAMPLE 5

Catalyst 7 was prepared and used to catalyze the reaction of ethylene oxide to monoethylene glycol in the same manner as Catalyst 1 in Example 1, except sebacic acid was used instead of terephthalic acid. Catalyst 7 had a monoethylene glycol selectivity of 95.5%, as shown in Table 1.

Catalyst 8 was prepared in the same manner as Catalyst 7, except without the calcination step. Catalyst 8 had a monoethylene glycol selectivity of 94.0%, as shown in Table 1.

EXAMPLE 6

Catalyst 9 was prepared and used to catalyze the reaction of ethylene oxide to monoethylene glycol in the same manner as Catalyst 1 in Example 1, except glutaric acid was used instead of terephthalic acid. Catalyst 9 had a monoethylene glycol selectivity of 95.1%, as shown in Table 1.

Catalyst 10 was prepared in the same manner as Catalyst 9, except without the calcination step. Catalyst 10 had a monoethylene glycol selectivity of 94.1%, as shown in Table 1.

EXAMPLE 8

For purposes of comparison, Catalyst 11, a hydrotalcite material wherein M is nickel, Q is aluminum and E is vanadate was prepared from a hydrotalcite wherein M is nickel, Q is aluminum and the interstitial anion is carbonate.

A 3 liter flask was flushed with $N_2$ for 30 minutes, and then equipped with a reflux condenser, temperature probe, mechanical stirrer, pressure equalizing addition funnel and nitrogen inlet. One liter of deionized water, 128 g of sodium hydroxide and 106 g of sodium carbonate were charged to the flask. The contents were stirred until dissolved and then cooled to room temperature.

A metal salt solution was prepared by adding 169 g of aluminum nitrate and 291 g of nickel nitrate to deionized water to make a 700 ml solution. The metal salt solution was charged to the addition funnel. The contents of the flask were heated to 40° C. and the metal salt solution was added to the flask with rapid stirring.

The resulting mixture was allowed to digest at 70° C. for 18 hours. It was then cooled to room temperature, suction filtered, washed with 600 ml of deionized water, and air dried. The resulting hydrotalcite was then calcined at 420° C. overnight, and the fines were separated.

A 3 liter flask was then flushed with $N_2$ for 30 minutes, and the calcined material was added thereto along with 1500 ml of deionized water. The pH was maintained in the range of 9 to 11. 122 g of sodium metavanadate were added to the flask and stirred gently for 4 days. The resulting hydrotalcite material was suction filtered, washed with deionized water and air dried.

Catalyst 11 was used to catalyze the reaction of ethylene oxide to monoethylene glycol in the same manner as Catalyst 1 in Example 1. Catalyst 11 had a monoethylene glycol selectivity of 95.1%, as shown in Table I.

TABLE 1

| Catalyst | Spacer | Calcine | MEG Sel (%) | mM Vanadate[7] | Cat Loading (%)[8] | Wt Cat (g) |
|---|---|---|---|---|---|---|
| 1 | Tere[1] | Yes | 97.0 | 8.3 | 17.2 | 13.07 |
| 2 | Tere | No | 95.3 | 27.5 | 108 | 10.51 |
| 3 | Cyclo[2] | Yes | 96.2 | 8.2 | 22 | 11.98 |
| 4 | Cyclo | No | 95.8 | 20.2 | 79.1 | 10.68 |
| 5 | Ben[3] | Yes | 95.8 | 13.0 | 22.8 | 16.51 |
| 6 | Ben | No | 94.9 | 41.7 | 86.8 | 16.20 |
| 7 | Seb[4] | Yes | 95.5 | 6.5 | 26 | 7.53 |
| 8 | Seb | No | 94.0 | 25.5 | 74.9 | 12.00 |
| 9 | Glut[5] | Yes | 95.1 | 9.3 | 13.2 | 19.70 |
| 10 | Glut | No | 94.1 | 18.2 | 97.8 | 12.11 |
| 11 | Carb[6] | Yes | 95.1 | 8.6 | 15.6 | 15.70 |
| Uncatalyzed | — | | 89.0 | — | — | |

[1]Tere = Terephthalate
[2]Cyclo = Cyclohexanecarboxylate
[3]Ben = Benzoate
[4]Seb = Sebacate
[5]Glut = Glutarate
[6]Carb = Carbonate
[7]mM Vanadate = millimoles of vanadate in the reactor
[8]Cat Loading (%) = % of anions in the hydrotalcite-type catalyst which were vanadate

EXAMPLE 7

For purposes of comparison, an uncatalyzed hydrolysis of ethylene oxide to monoethylene glycol was carried in the same manner as in Example 1, except without any catalyst in the tube.

Table 1 shows that the uncatalyzed hydrolysis reaction had a selectivity of 89.0% to monoethylene glycol.

EXAMPLE 9

Catalyst 12 was prepared and used to catalyze the reaction of ethylene oxide to monoethylene glycol in the same manner as Catalyst 2 in Example 2 (that is, uncalcined), except 115 g of sodium molybdate were used instead of 122 g of sodium metavanadate. Catalyst 12 had a monoethylene glycol selectivity of 93.9%.

EXAMPLE 10

Catalyst 13 was prepared and used to catalyze the reaction of ethylene oxide to monoethylene glycol in the same manner as Catalyst 1 in Example 1 (that is, calcined), except 106 g of sodium tungstate were used instead of 122 g of sodium metavanadate. Catalyst 13 had a monoethylene glycol selectivity of 93.9%.

EXAMPLE 11

This example illustrates the synthesis of hydrotalcite-type catalysts according to the invention, wherein M is nickel, Q is aluminum, and E is niobate from a hydrotalcite-type composition wherein M is nickel, Q is aluminum and A is benzoate.

This catalyst was designated Catalyst 14 and was prepared in the same manner as Catalyst 1 in Example 1, using 75 g of potassium hydroxide, 32 g of sodium benzoate, 63 g of aluminum nitrate, 117 g of nickel nitrate and 7.5 g of potassium niobate. Catalyst 14 was used to catalyze the reaction of ethylene oxide to ethylene glycol as in Example 1. Catalyst 14 had a selectivity to monoethylene glycol of 97.1%.

Catalyst 15 was prepared in the same manner as Catalyst 14 except the hydrotalcite-type composition was not calcined before it was contacted with the potassium niobate. The monoethylene glycol selectivity of Catalyst 15 was 92.8%.

EXAMPLE 12

Catalyst 16 was prepared and used to catalyze the reaction of ethylene oxide to ethylene glycol in the same manner as Catalyst 14 in Example 1, except sodium carbonate was used instead of sodium benzoate. Catalyst 16 had a monoethylene glycol selectivity of 94.6%.

EXAMPLE 13

Catalyst 17 was prepared and used to catalyze the reaction of ethylene oxide to ethylene glycol in the same manner as Catalyst 14 in Example 11, except 9.1 g of potassium tantalate were used instead of 7.5 g of potassium niobate.

Catalyst 17 had a monoethylene glycol selectivity of 94.6%

EXAMPLE 14

This example illustrates the synthesis of a hydrotalcite-type catalyst according to the invention, wherein M is a mixture of copper and nickel, Q is aluminum and E is vanadate from a hydrotalcite-type composition wherein M is a mixture of copper and nickel, Q is aluminum and A is benzoate.

This catalyst was designated Catalyst 18 and was prepared in the same manner as Catalyst 1 in Example 1, using 128 g of sodium hydroxide, 88 g of sodium benzoate, 47 g of copper nitrate, 233 g of nickel nitrate, 187 g of aluminum nitrate and 122 g of sodium metavanadate. Catalyst 18 was used to catalyze the hydrolysis of ethylene oxide to ethylene glycol as in Example 1. Catalyst 18 had a selectivity to monoethylene glycol of 94.7%.

EXAMPLE 15

This example illustrates the synthesis of a hydrotalcite-type catalyst according to the invention, wherein M is nickel, Q is a mixture of lanthanum and aluminum and E is vanadate from a hydrotalcite-type composition wherein M is nickel, Q is a mixture of lanthanum and aluminum and A is terephthalate.

This catalyst was designated Catalyst 19 and was prepared in the same manner as Catalyst 1 in Example 1 using 88 g of sodium hydroxide, 34 g of terephthalic acid, 160 g of nickel nitrate, 12 g of lanthanum nitrate, 93 g of aluminum nitrate and 40 g of sodium metavanadate. Catalyst 19 was used to catalyze the hydrolysis of ethylene oxide to ethylene glycol as in Example 1. Catalyst 19 had a selectivity to monoethylene glycol of 94.6%.

EXAMPLE 16

This example illustrates the synthesis of a hydrotalcite-type catalyst according to the invention, wherein M is nickel, Q is chromium and E is vanadate from a hydrotalcite-type composition wherein M is nickel, Q is chromium and A is terephthalate.

This catalyst was designated Catalyst 20 and was prepared in the same manner as Catalyst 1 in Example 1, using 69 g of sodium hydroxide, 32 g of terephthalic acid, 117 g of nickel nitrate, 80 g of chromium nitrate and 50 g of sodium metavanadate. Catalyst 20 was used to catalyze the hydrolysis of ethylene oxide to ethylene glycol as in Example 1. Catalyst 20 had a selectivity to monoethylene glycol of 92.9%.

EXAMPLE 17

This example illustrates the synthesis of a hydrotalcite-type catalyst according to the invention, wherein M is magnesium, Q is aluminum and E is vanadate from a hydrotalcite-type composition wherein M is magnesium, Q is aluminum and A is terephthalate.

This catalyst was designated Catalyst 21 and was prepared in the same manner as Catalyst 1 in Example 1 using 72 g of sodium hydroxide, 33 g of terephthalic acid, 105 g of magnesium nitrate, 75 g of aluminum nitrate and 100 g of sodium metavanadate. Catalyst 21 was used to catalyze the hydrolysis of ethylene oxide to ethylene glycol as in Example 1. Catalyst 21 had a selectivity to monoethylene glycol of 94.8%.

EXAMPLE 18

This example illustrates the synthesis of a hydrotalcite-type catalyst according to the invention, wherein M is titanium, Q is aluminum and E is vanadate from a hydrotalcite-type composition wherein M is titanium, Q is aluminum and A is benzoate.

This catalyst is designated Catalyst 22 and is prepared as follows. A solution of 20 g of titanium (IV) chloride and 250 g of aluminum chloride in 500 ml water is added to a solution containing 15 g of benzoic acid in one liter of water heated to 70° C. The pH of the mixture is maintained in the range of 5 to 5.5 by the addition of sodium hydroxide. The mixture is stirred for an additional hour and then filtered and washed with water. The mixture is then suspended in 800 ml of water, the pH is raised to the range of 9 to 10 with sodium hydroxide, and 15 g of sodium metavanadate are added. The resulting slurry is stirred for 18 hours and the resulting hydrotalcite-type catalyst is filtered and washed with water.

EXAMPLE 19

This Example illustrates the synthesis of a hydrotalcite-type catalyst according to the invention, wherein M is titanium, Q is aluminum and E is molybdate, from a hydrotalcite-type composition wherein M is titanium, Q is aluminum and A is benzoate.

This catalyst is designated Catalyst 23, and is prepared in the same manner as Catalyst 22 in Example 18, except that 15 g of sodium molybdate are used instead of 15 g of sodium metavanadate.

We claim:

1. A process for producing monoalkylene glycol, which comprises
   (a) preparing a hydrotalcite-type composition of the formula $$M_xQ_y(OH)_{2x+3y-nz}A^{n-}{}_z \cdot a\ H_2O$$

wherein M is at least one divalent metal cation; Q is at least one trivalent metal cation; A is at least one large organic anion spacer having a valence $n^-$ selected from the group consisting of terephthalate, benzoate, cyclohexanecarboxylate, sebacate, glutarate, acetate and mixtures thereof; a is a positive number; M, Q and A are present such that x/y is a number equal to or greater than 1, z has a value greater than zero, $2x+3y-nz$ is a positive number, and the composition has a layered structure; A being located in anionic sites in the composition;
   (b) contacting the composition of step (a) with a solution containing a metalate anion, whereby at least some of the large organic anion spacer in the anionic sites of the composition is replaced by the metalate anion; and
   (c) reacting alkylene oxide with water in the presence of the metalate-substituted composition of step (b) to form monoalkylene glycol.

2. The process of claim 1, wherein said large organic anion spacer is terephthalate.

3. The process of claim 1, wherein the metalate anion is selected from the group consisting of vanadate, molybdate, tungstate, niobate, tantalate, perrhenate and mixtures thereof.

4. The process of claim 1, wherein the metalate anion comprises vanadate.

5. The process of claim 1, wherein the metalate anion comprises niobate.

6. The process of claim 1, wherein said calcination takes place by heating at a temperature of 300° C. to 600° C.

7. The process of claim 1, wherein M is selected from the group consisting of magnesium, nickel, cobalt, zinc, calcium, iron, titanium, copper and mixtures thereof.

8. The process of claim 1 wherein M is selected from the group consisting of magnesium and nickel.

9. The process of claim 1 wherein Q is selected from the group consisting of aluminum, lanthanum, chromium, iron and mixtures thereof.

10. The process of claim 1, wherein M is nickel, Q is aluminum and the metalate anion is vanadate.

11. The process of claim 1, wherein M is nickel, Q is aluminum and the metalate anion is niobate.

12. The process of claim 1, wherein at least about 25 molar % of the anionic sites of the composition are loaded with the metalate anion after contacting.

13. The process of claim 1, wherein at least about 1 molar % of the anionic sites of the composition are loaded with the metalate anion after contacting.

14. The process of claim 1, wherein the monoalkylene glycol is monoethylene glycol and the alkylene oxide is ethylene oxide.

15. The process of claim 1, wherein the monoalkylene glycol is monopropylene glycol and the alkylene oxide is propylene oxide.

* * * * *